US011361841B2

(12) United States Patent
Nguyen et al.

(10) Patent No.: US 11,361,841 B2
(45) Date of Patent: Jun. 14, 2022

(54) HIGH-THROUGHPUT IDENTIFICATION OF PATIENT-SPECIFIC NEOEPITOPES AS THERAPEUTIC TARGETS FOR CANCER IMMUNOTHERAPIES

(71) Applicants: NantOmics, LLC, Culver City, CA (US); Nant Holdings IP, LLC, Culver City, CA (US)

(72) Inventors: Andrew Nguyen, Culver City, CA (US); John Zachary Sanborn, Culver City, CA (US); Stephen Charles Benz, Santa Cruz, CA (US); Kayvan Niazi, Culver City, CA (US); Shahrooz Rabizadeh, Culver City, CA (US); Patrick Soon-Shiong, Culver City, CA (US); Charles Joseph Vaske, Culver City, CA (US)

(73) Assignee: Nantomics LLC, Culver City, CA (US)

( * ) Notice: Subject to any disclaimer, the term of this patent is extended or adjusted under 35 U.S.C. 154(b) by 568 days.

(21) Appl. No.: 16/073,105

(22) PCT Filed: Feb. 10, 2017

(86) PCT No.: PCT/US2017/017549
§ 371 (c)(1),
(2) Date: Jul. 26, 2018

(87) PCT Pub. No.: WO2017/139694
PCT Pub. Date: Aug. 17, 2017

(65) Prior Publication Data
US 2019/0034582 A1 Jan. 31, 2019

Related U.S. Application Data

(60) Provisional application No. 62/294,665, filed on Feb. 12, 2016.

(51) Int. Cl.
| | |
|---|---|
| *G16B 20/20* | (2019.01) |
| *G16B 20/00* | (2019.01) |
| *A61K 35/17* | (2015.01) |
| *A61K 39/395* | (2006.01) |
| *A61K 48/00* | (2006.01) |
| *C12Q 1/6886* | (2018.01) |
| *A61K 47/68* | (2017.01) |
| *A61K 39/00* | (2006.01) |
| *A61K 45/06* | (2006.01) |

(52) U.S. Cl.
CPC ............ *G16B 20/20* (2019.02); *A61K 35/17* (2013.01); *A61K 39/0011* (2013.01); *A61K 39/395* (2013.01); *A61K 39/39558* (2013.01); *A61K 45/06* (2013.01); *A61K 47/6851* (2017.08); *A61K 48/00* (2013.01); *C12Q 1/6886* (2013.01); *G16B 20/00* (2019.02); *A61K 39/00* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 7,473,532 | B2 | 1/2009 | Drafler et al. |
| 8,119,117 | B2 | 2/2012 | Deisseroth et al. |
| 2008/0267999 | A1 | 10/2008 | Tainsky et al. |
| 2012/0059670 | A1 | 3/2012 | Sanborn et al. |
| 2012/0059760 | A1 | 3/2012 | Sanborn et al. |
| 2012/0066001 | A1 | 3/2012 | Sanborn et al. |
| 2016/0101170 | A1* | 4/2016 | Hacohen ................ A61K 39/39 |
| | | | 424/277.1 |
| 2016/0339090 | A1* | 11/2016 | Hacohen ............ A61K 39/3955 |
| 2017/0017749 | A1 | 1/2017 | Carmeli et al. |
| 2017/0028043 | A1 | 2/2017 | Benz et al. |

FOREIGN PATENT DOCUMENTS

| CA | 3 014 252 A1 | 8/2017 |
| CN | 108701172 A | 10/2018 |
| JP | 2013-530943 A | 8/2013 |
| JP | 2015-533473 A | 11/2015 |
| JP | 2019-511907 A | 5/2019 |
| KR | 10-2018-0091119 A | 8/2018 |
| MX | 2018009804 A | 11/2018 |
| WO | 2011143656 A2 | 11/2011 |
| WO | 2014012051 | 1/2014 |
| WO | 2014/168874 A2 | 10/2014 |
| WO | 2014/168874 A3 | 10/2014 |
| WO | 2014/168874 A3 | 12/2014 |
| WO | 2015/095811 A2 | 6/2015 |
| WO | 2016/172722 A1 | 10/2016 |
| WO | 2017/035392 A1 | 3/2017 |

(Continued)

OTHER PUBLICATIONS

Lundegaard et al. "Prediction of epitopes using neural network based methods" in J Immunol Methods 374:26 (2011).*
Rubio-Perez et al. in Cancer Cell (2015) vol. 27:382-396).*
Notice of reason of rejection received for Japanese Application Serial No. JP2018-542278, dated Nov. 14, 2019, 14 pages.
Office Action received for Canadian Patent Application Serial No. 3014252 dated May 7, 2019, 4 pages.
Office Action received for Canadian Patent Application Serial No. 3014252 dated Apr. 3, 2020, 4 pages.
Communication pursuant to Rule 164(1) EPC received for European Patent Application Serial No. 17750909.8 dated Feb. 25, 2020, 13 pages.

(Continued)

*Primary Examiner* — Lori A. Clow
(74) *Attorney, Agent, or Firm* — Martin Fessenmaier; Umberg Zipser LLP

(57) ABSTRACT

Systems and methods are presented that allow for selection of tumor neoepitopes that are filtered for various criteria. In particularly contemplated aspects, filtering includes a step in which the mutation leading to the neoepitope is ascertained as being located in a cancer driver gene.

12 Claims, 2 Drawing Sheets

(56) References Cited

FOREIGN PATENT DOCUMENTS

| WO | 2017066357 A1 | 4/2017 |
|---|---|---|
| WO | 2017/139694 A1 | 8/2017 |

OTHER PUBLICATIONS

Hacohen et al., "Getting Personal with Neoantigen-Based Therapeutic Cancer Vaccines", Cancer Immunology Research, 2013, pp. 11-15.
Lu et al., "Cancer immunotherapy targeting neoantigens", Seminars in Immunology, vol. 28, No. 1, pp. 11-16.
International Search Report and Written Opinion received for PCT Application Serial No. PCT/US2017/017549 dated May 22, 2017, 14 pages.
International Preliminary Reporton Patentability Chapter I received for PCT Application Serial No. PCT/US2017/017549 dated Aug. 23, 2018, 12 pages.
Sykulev et al., "Evidence that a single peptide-MHC complex on a target cell can elicit a cytolytic T cell response", Immunity, 1996, vol. 4, No. 6, pp. 565-571 (Cited from Specification).
Lundegaard et al., "NetMHC-3.0: accurate web accessible predictions of human, mouse and monkey MHC class I affinities for peptides of length 8-11", Nucleic Acids Research, 2008, vol. 36, pp. W509-W512 (Cited from Specification).
Zhang et al., "Machine learning competition in immunology—Prediction of HLA class I binding peptides", Journal of Immunological Methods, 2011, vol. 374, pp. 1-4 (Cited from Specification).
Lawrence et al., "Discovery and saturation analysis of cancer genes across 21 tumour types", Nature, 2014, vol. 505, No. 7484, 22 pages (Cited from Specification).
Reimand et al., "Systematic analysis of somatic mutations in phosphorylation signaling predicts novel cancer drivers", Molecular Systems Biology, 2013, vol. 9, No. 637, pp. 1-18 (Cited from Specification).
Dees et al., "MuSiC: identifying mutational significance in cancer genomes", Genome Research, 2012, vol. 22, pp. 1589-1598 (Cited from Specification).
Tamborero et al., "OncodriveCLUST: exploiting the positional clustering of somatic mutations to identify cancer genes", Bioinformatics, 2013, vol. 29, No. 18, pp. 2238-2244 (Cited from Specification).
Gonzalez-Perez et al., "Functional impact bias reveals cancer drivers", Nucleic Acids Research, 2012, vol. 40, No. 21, pp. 1-10 (Cited from Specification).
Mularoni et al., "OncodriveFML: a general framework to identify coding and non-coding regions with cancer driver mutations", Genome Biology, 2016, vol. 17, No. 128, pp. 1-13 (Cited from Specification).
Davoli et al., "Cumulative Haploinsufficiency and Triplosensitivity Drive Aneuploidy Patterns and Shape the Cancer Genome", Cell, 2013, vol. 155, pp. 948-962 (Cited from Specification).
Schroeder et al., "OncodriveROLE classifies cancer driver genes in loss of function and activating mode of action", Bioinformatics, 2014, vol. 30, pp. i549-i555 (Cited from Specification).
Vaske et al., "Inference of patient-specific pathway activities from multi-dimensional cancer genomics data using PARADIGM", Bioinformatics, 2010, vol. 26, pp. i237-i245 (Cited from Specification).
Ng et al., "PARADIGM-SHIFT predicts the function of mutations in multiple cancers using pathway impact analysis", Bioinformatics, 2012, vol. 28, pp. i640-i646 (Cited from Specification).
Rubio-Perez et al., "In silico prescription of anticancer drugs to cohorts of 28 tumor types reveals targeting opportunities", Cancer Cell, 2015, vol. 27, pp. 382-396 (Cited from Specification).
Amalfitano et al., "Production and Characterization of Improved Adenovirus Vectors with the E1, E2b, and E3 Genes Deleted", Journal of Virology, 1998, vol. 72, No. 2, pp. 926-933 (Cited from Specification).
Rajasagi et al., "Systematic identification of personal tumor-specific neoantigens in chronic lymphocytic leukemia", BLOOD, vol. 124, No. 3, Jul. 17, 2014, 11 pages.
Segal et al., "Epitope Landscape in Breast and Colorectal Cancer", Cancer Res 2008, vol. 68, No. 3, Feb. 1, 2008, 5 pages.
Carreno et al., "A dendritic cell vaccine increases the breadth and diversity of melanoma neoantigen-specific T cells", SCIENCE, vol. 348, No. 6236, May 15, 2015, 8 pages.
Dancey et al., "The Genetic Basis for Cancer Treatment Decisions", Cell, vol. 148, Feb. 3, 2012, pp. 409-420.
Written Opinion received in SG Application No. 11201806282X, dated Sep. 2, 2019, 8 pages.
Extended European Search Report received for European Patent Application Serial No. 17750909.8 dated Jun. 25, 2020, 13 pages.
Notice of Reasons for Refusal received for Japanese Patent Application Serial No. 2018-542278 dated Jun. 23, 2020, 12 pages (Including English Translation).
Notice of Reasons for Refusal received for Korean Patent Application Serial No. 10-2018-70225278 dated Jun. 10, 2020, 08 pages (Including English Translation).
Boegel et al., "A catalog of HLA type, HLA expression, and neoepitope candidates in human cancer cell lines", OncoImmunology, Aug. 1, 2014, vol. 3, No. 8, pp. e954893-1-e954893-12.

* cited by examiner

HIGH-THROUGHPUT IDENTIFICATION OF PATIENT-SPECIFIC NEOEPITOPES AS THERAPEUTIC TARGETS FOR CANCER IMMUNOTHERAPIES

This application claims priority to U.S. provisional application with the Ser. No. 62/294,665, filed Feb. 12, 2016, and which is incorporated by reference herein.

FIELD OF THE INVENTION

The field of the invention is computational analysis of omics data to predict treatment options, especially as it relates to selection of target epitopes in neoepitope-based immune therapy.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer immunotherapies targeting certain antigens common to a specific cancer have led to remarkable responses in some patients. Unfortunately, many patients failed to respond to such immunotherapy despite apparent expression of the same antigen. One possible reason for such failure could be that various effector cells of the immune system may not have been present in sufficient quantities, or may have been exhausted. Moreover, intracellular antigen processing and HLA variability among patients may have led to insufficient processing of the antigen and/or antigen display, leading to a therapeutically ineffective or lacking response.

To increase the selection of targets for immune therapy, random mutations have more recently been considered since some random mutations in tumor cells may give rise to unique tumor specific antigens (neoepitopes). As such, and at least conceptually, neoepitopes may provide a unique precision target for immunotherapy. Additionally, it has been shown that cytolytic T-cell responses can be triggered by very small quantities of peptides (e.g., Sykulev et al., *Immunity*, Volume 4, Issue 6, p565-571, 1 Jun. 1996). Moreover, due to the relatively large number of mutations in many cancers, the number of possible targets is relatively high. In view of these findings, the identification of cancer neoepitopes as therapeutic targets has attracted much attention. Unfortunately, current data appear to suggest that all or almost all cancer neoepitopes are unique to a patient and specific tumor and therefore fail to provide any specific indication as to which neoepitope may be useful for an immunotherapeutic agent that is therapeutically effective.

To overcome at least some of the problems associated with large numbers of possible targets for immune therapy, the neoepitopes can be filtered for the type of mutation (e.g., to ascertain missense or nonsense mutation), the level of transcription to confirm transcription of the mutated gene, and to confirm protein expression. Moreover, the so filtered neoepitope may be further analyzed for specific binding to the patient's HLA system as described in WO 2016/172722. While such system advantageously reduces the relatively large number of potential neoepitopes, the significance of these neoepitopes with respect to treatment outcome remains uncertain.

Thus, even though multiple methods of identification of neoepitopes are known in the art, all or almost all of them suffer from one or more disadvantage. Consequently, it would be desirable to have improved systems and methods for neoepitope identification that increases the likelihood of a therapeutic response in immune therapy.

SUMMARY OF THE INVENTION

The inventive subject matter is directed to various composition and methods for selecting neoepitopes for immune therapy targeting neoepitopes that are not only expressed and presented on a tumor cell, but that also confer a functional advantage to the tumor cell. Most preferably, contemplated neoepitopes will include cancer driver mutations. As such, contemplated compositions and methods will subject tumor cells and their mutated drivers to humoral and cellular immune response and so increase the likelihood of therapeutic effect.

In one aspect of the inventive subject matter, the inventors contemplate a method of selecting a neoepitope for immune therapy of a cancer that includes a step of obtaining from a patient omics data from a tumor tissue and a matched normal tissue, and using the omics data to determine a plurality of expressed missense based patient- and tumor-specific neoepitopes. In a further step, the expressed missense based patient- and tumor-specific neoepitopes are filtered by HLA type of the patient to thereby obtain HLA-matched neoepitopes, and in a still further step, the HLA-matched neoepitopes are filtered by a gene type that is affected by the HLA-matched neoepitopes to thereby obtain a cancer driver neoepitope.

It such methods, it is further contemplated that the omics data comprise at least two omics data selected from the group consisting of whole genome sequencing data, whole exome sequencing data, RNAseq data, and quantitative proteomics data, and/or that the step of determining the plurality of expressed missense based patient- and tumor-specific neoepitopes comprises location-guided synchronous alignment of omics data from the tumor tissue and the matched normal tissue. Where desired, contemplated methods may further comprise a step of filtering the expressed missense based patient- and tumor-specific neoepitopes by at least one of an a priori known molecular variation selected from the group consisting of a single nucleotide polymorphism, a short deletion and insertion polymorphism, a microsatellite marker, a short tandem repeat, a heterozygous sequence, a multinucleotide polymorphism, and a named variant. Most typically, the tumor tissue is a solid tumor tissue and the matched normal tissue is blood.

Advantageously, the step of filtering the patient- and tumor-specific neoepitopes by HLA type may be performed for each of the neoepitopes using a plurality of distinct individual neoepitope sequences in which a changed amino acid has a distinct position within the neoepitope sequence. For example, individual neoepitope sequences may have a length of between 7 and 20 amino acids.

It is further contemplated that the step of filtering by HLA type may include a determination of the HLA type from the patient omics data. Typically, but not necessarily, the step of filtering by HLA type is performed to a depth of at least 2 digits, and more typically at least 4 digits. Additionally, or alternatively, the step of filtering by HLA type may also comprise a determination of affinity of the neoepitopes to at least one MHC Class I sub-type and to at least one MHC Class II sub-type of the patient. For example, HLA-matched neoepitopes may have an affinity to at least one MHC Class I sub-type or to at least one MHC Class II sub-type of the patient of equal or less than 150 nM.

With respect to the gene type affected, it is generally contemplated that the gene type is a cancer driver and/or passenger gene, typically for a cancer selected from the group consisting of ALL, AML, BLCA, BRCA, CLL, CM, COREAD, ESCA, GBM, HC, HNSC, LUAD, LUSC, MB, NB, NSCLC, OV, PRAD, RCCC, SCLC, STAD, THCA, and UCEC. For example, suitable cancer driver genes are listed in Table 1.

Where desired, suitable methods may further comprise a step of determining a malfunction in the affected cancer driver gene. In such case, a recommendation may be generated for a non-immune therapeutic drug that targets a protein encoded by the affected cancer driver gene. Moreover, it is also contemplated that the methods presented herein may further include a step of using the cancer driver neoepitope to prepare an immune therapeutic agent. For example, suitable immune therapeutic agents may comprise at least one of a synthetic antibody having binding specificity to the cancer driver neoepitope, a synthetic cancer driver neoepitope, a nucleic acid encoding the cancer driver neoepitope, an immune competent cell carrying a chimeric antigen receptor having binding specificity to the cancer driver neoepitope, and a recombinant virus comprising a nucleic acid encoding the cancer driver neoepitope.

Therefore, the inventors also contemplate a method of treating a cancer in a patient using immune therapy. Such methods will include a step of obtaining from a patient omics data from a tumor tissue and a matched normal tissue, and using the omics data to determine a plurality of expressed missense based patient- and tumor-specific neoepitopes. In another step, a cancer driver neoepitope is derived from the expressed missense based patient- and tumor-specific neoepitopes. In yet another step, an immune therapeutic agent is administered to the patient that comprises at least one of a synthetic antibody having binding specificity to the cancer driver neoepitope, a synthetic cancer driver neoepitope, a nucleic acid encoding the cancer driver neoepitope, an immune competent cell carrying a chimeric antigen receptor having binding specificity to the cancer driver neoepitope, and a recombinant virus comprising a nucleic acid encoding the cancer driver neoepitope.

As before, it is contemplated that the omics data will typically comprise at least two omics data selected from the group consisting of whole genome sequencing data, whole exome sequencing data, RNAseq data, and quantitative proteomics data, and/or that the step of determining the plurality of expressed missense based patient- and tumor-specific neoepitopes may comprise location-guided synchronous alignment of omics data from the tumor tissue and the matched normal tissue. Contemplated methods may also include a further step of filtering the expressed missense based patient- and tumor-specific neoepitopes by at least one of an a priori known molecular variation selected from the group consisting of a single nucleotide polymorphism, a short deletion and insertion polymorphism, a microsatellite marker, a short tandem repeat, a heterozygous sequence, a multinucleotide polymorphism, and a named variant.

Typically, but not necessarily, the step of deriving the cancer driver neoepitope will include a step of filtering the patient- and tumor-specific neoepitopes by HLA type of the patient (which may use a plurality of distinct individual neoepitope sequences in which a changed amino acid has a distinct position within the neoepitope sequence, wherein the individual neoepitope sequences may have a length of between 7 and 20 amino acids). Moreover, the step of filtering by HLA type may comprise a determination of the HLA type from the patient omics data, and/or may be performed to a depth of at least 4 digits, and/or may comprise a determination of affinity of the neoepitopes to at least one MHC Class I sub-type and to at least one MHC Class II sub-type of the patient.

Contemplated cancer driver neoepitopes may be located in a gene selected from the group consisting of ALL, AML, BLCA, BRCA, CLL, CM, COREAD, ESCA, GBM, HC, HNSC, LUAD, LUSC, MB, NB, NSCLC, OV, PRAD, RCCC, SCLC, STAD, THCA, and UCEC, and exemplary cancer driver genes are listed in Table 1. In addition, contemplated methods may include a step of administering a non-immune therapeutic drug that targets a protein comprising the cancer driver neoepitope.

Consequently, the inventors also contemplate an immune therapeutic composition that comprises a carrier coupled to (i) a synthetic antibody having binding specificity to a patient specific cancer driver neoepitope, (ii) a synthetic patient specific cancer driver neoepitope, (iii) a nucleic acid encoding the patient specific cancer driver neoepitope, or (iv) a chimeric antigen receptor having binding specificity to the patient specific cancer driver neoepitope.

Suitable carriers may include a single protein or may comprise a pharmaceutically acceptable polymer. Alternatively, the carrier may also be an immune competent cell (e.g., a CD8+ T cell or a NK cell) or a recombinant virus. As desired, a pharmaceutically acceptable carrier suitable for injection or infusion may be included.

Thus, and viewed from a different perspective, the inventors also contemplate the use of an immune therapeutic agent in the treatment of a cancer, wherein the immune therapeutic agent comprises at least one of a synthetic antibody having binding specificity to a patient specific cancer driver neoepitope, a synthetic patient specific cancer driver neoepitope, a nucleic acid encoding a patient specific cancer driver neoepitope, an immune competent cell carrying a chimeric antigen receptor having binding specificity to a patient specific cancer driver neoepitope, and a recombinant virus comprising a nucleic acid encoding a patient specific cancer driver neoepitope.

For example, the synthetic antibody may be coupled to an NK cell or to a carrier comprising a single protein or comprising a pharmaceutically acceptable polymer, and/or the patient specific synthetic cancer driver neoepitope may be coupled to a carrier comprising a single protein or comprising a pharmaceutically acceptable polymer. Alternatively, the nucleic acid encoding the patient specific cancer driver neoepitope may be contained in an immune competent cell or in a virus, or coupled to a carrier comprising a single protein or comprising a pharmaceutically acceptable polymer.

Consequently, the inventors also contemplate a recombinant immune competent cell (e.g., CD8+ T cell or a NK cell, or an NK92 derivative) comprising a nucleic acid encoding a chimeric antigen receptor having binding specificity to a patient specific cancer driver neoepitope, or encoding the patient specific cancer driver neoepitope.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
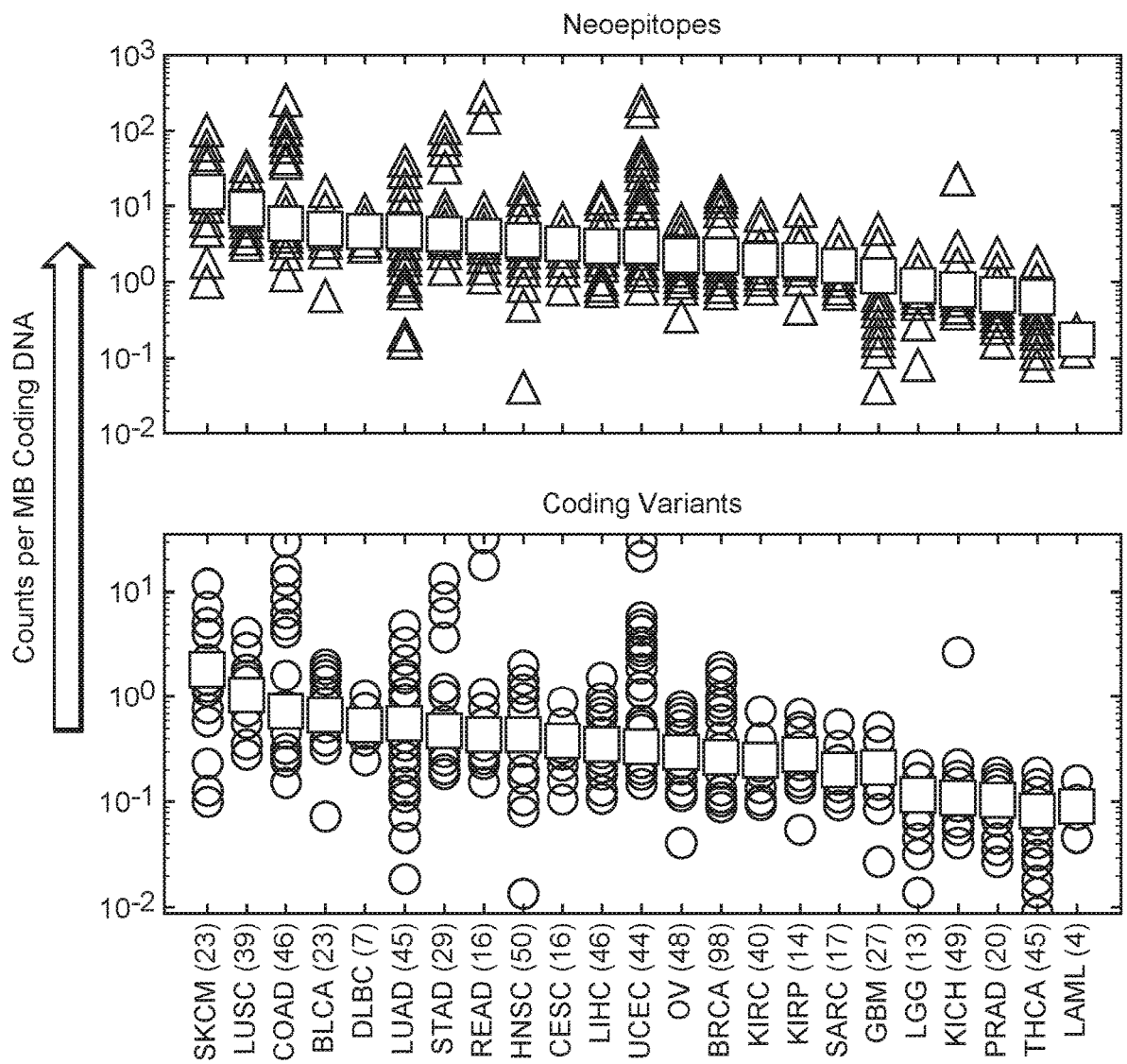
FIG. 1 is an exemplary graphical representation of neoepitope frequency and coding variant frequency across various cancers, as well as a graphical representation of frequency of unique neoepitopes across various cancers.
Figure 1:
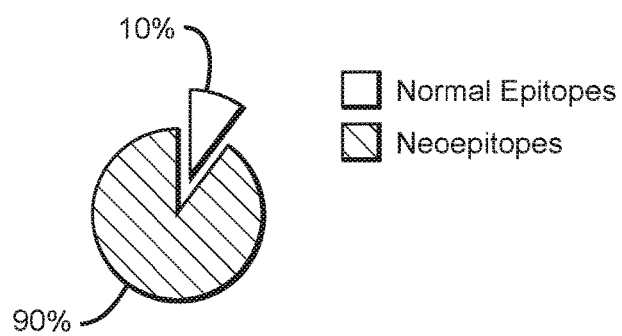

The inventors have now discovered that neoepitope-based immune therapy can be further improved by targeting expressed patient- and tumor specific neoepitopes that confer a functional advantage to the tumor cell. Most preferably, the neoepitopes will be located in a protein that is encoded by a known, predicted, or suspected cancer driver gene. Consequently, it is contemplated that an immune response against such cancer driver neoepitope will not only result in a cytotoxic immune response, but also in a humoral response directed against the cancer driver proteins. For example, where the cancer driver gene is KIT (mast/stem cell growth factor receptor) and includes a neoepitope, an antibody binding to the KIT neoepitope may not only tag the protein for cytotoxic destruction by NK and T cells, but may also inhibit signaling through the receptor pathway and as such inhibit cancer driver function.

To that end, it is contemplated that the cancer driver neoepitopes can be identified in a process that preferably uses patient tumor material (e.g., biopsy sample) and matched normal tissue (non-tumor, typically healthy tissue of the same patient). Omics analysis can then be performed on the patient samples to obtain omics data, most typically genomics data (such as whole genome sequence data, whole exome data, etc.), transcriptomics data (and especially RNAseq data), and/or proteomics data (which may be qualitative or quantitative). The omics data can then be used to identify and filter (expressed and HLA-matched patient- and tumor specific) cancer driver neoepitopes as is described in more detail below. So identified cancer driver neoepitopes can then be used in immune therapy using various treatment modalities, including cell based treatments, cancer vaccines, therapeutic antibodies, etc.

Neoepitopes can be characterized as expressed random mutations in tumor cells that created unique and tumor specific antigens. Therefore, viewed from a different perspective, neoepitopes may be identified by considering the type (e.g., deletion, insertion, transversion, transition, translocation) and impact of the mutation (e.g., non-sense, missense, frame shift, etc.), which may as such serve as a first content filter through which silent and other non-relevant (e.g., non-expressed) mutations are eliminated. It should further be appreciated that neoepitope sequences can be defined as sequence stretches with relatively short length (e.g., 7-11 mers) wherein such stretches will include the change(s) in the amino acid sequences. Most typically, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic amino acid and N is a changed amino acid (relative to wild type or relative to matched normal). For example, neoepitope sequences as contemplated herein include sequence stretches with relatively short length (e.g., 5-30 mers, more typically 7-11 mers, or 12-25 mers) wherein such stretches include the change(s) in the amino acid sequences.

Thus, it should be appreciated that a single amino acid change may be presented in numerous neoepitope sequences that include the changed amino acid, depending on the position of the changed amino acid. Advantageously, such sequence variability allows for multiple choices of neoepitopes and so increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 9-15 amino acids, with a changed amino acid preferably centrally located or otherwise situated in a manner that improves its binding to MHC. For example, where the epitope is to be presented by the MHC-I complex, a typical neoepitope length will be about 8-11 amino acids, while the typical neoepitope length for presentation via MHC-II complex will have a length of about 13-17 amino acids. As will be readily appreciated, since the position of the changed amino acid in the neoepitope may be other than central, the actual peptide sequence and with that actual topology of the neoepitope may vary considerably.

Of course, it should be appreciated that the identification or discovery of neoepitopes may start with a variety of biological materials, including fresh biopsies, frozen or otherwise preserved tissue or cell samples, circulating tumor cells, exosomes, various body fluids (and especially blood), etc. Therefore, suitable methods of omics analysis include nucleic acid sequencing, and particularly NGS methods operating on DNA (e.g., Illumina sequencing, ion torrent sequencing, 454 pyrosequencing, nanopore sequencing, etc.), RNA sequencing (e.g., RNAseq, reverse transcription based sequencing, etc.), and protein sequencing or mass spectroscopy based sequencing (e.g., SRM, MRM, CRM, etc.).

As such, and particularly for nucleic acid based sequencing, it should be particularly recognized that high-throughput genome sequencing of a tumor tissue will allow for rapid identification of neoepitopes. However, it must be appreciated that where the so obtained sequence information is compared against a standard reference, the normally occurring inter-patient variation (e.g., due to SNPs, short indels, different number of repeats, etc.) as well as heterozygosity will result in a relatively large number of potential false positive neoepitopes. Notably, such inaccuracies can be eliminated where a tumor sample of a patient is compared against a matched normal (i.e., non-tumor) sample of the same patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination. Therefore, data sets may include unprocessed or processed data sets, and exemplary data sets include those having BAMBAM format, SAMBAM format, FASTQ format, or FASTA format. However, it is especially preferred that the data sets are provided in BAMBAM format or as BAMBAM diff objects (see e.g., US2012/0059670A1 and US2012/0066001A1). Moreover, it should be noted that the data sets are reflective of a tumor and a matched normal sample of the same patient to so obtain patient and tumor specific information. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor or metastatic site, etc. In most cases, the matched normal sample of the patient may be blood, or non-diseased tissue from the same tissue type as the tumor.

Likewise, the computational analysis of the sequence data may be performed in numerous manners. In most preferred methods, however, analysis is performed in silico by location-guided synchronous alignment of tumor and normal samples as, for example, disclosed in US 2012/0059670A1 and US 2012/0066001A1 using BAM files and BAM servers. Such analysis advantageously reduces false positive neoepitopes and significantly reduces demands on memory and computational resources.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Viewed from a different perspective, a patient- and cancer-specific in silico collection of sequences can be established that have a predetermined length of between 5 and 25 amino acids and include at least one changed amino acid. Such collection will typically include for each changed amino acid at least two, at least three, at least four, at least five, or at least six members in which the position of the changed amino acid is not identical. Such collection can then be used for further filtering (e.g., by sub-cellular location, transcription/expression level, MHC-I and/or II affinity, etc.) as is described in more detail below.

For example, and using synchronous location guided analysis to tumor and matched normal sequence data, the inventors previously identified various cancer neoepitopes from a variety of cancers and patients, including the following cancer types: BLCA, BRCA, CESC, COAD, DLBC, GBM, HNSC, KICH, KIRC, KIRP, LAML, LGG, LIHC, LUAD, LUSC, OV, PRAD, READ, SARC, SKCM, STAD, THCA, and UCEC. All neoepitope data can be found in International application PCT/US16/29244, incorporated by reference herein.

Depending on the type and stage of the cancer, it should be noted that not all of the identified neoepitopes will necessarily lead to a therapeutically equally effective reaction in a patient when checkpoint inhibitors are given to a patient. Indeed, it is well known in the art that only a fraction of neoepitopes will generate an immune response. To increase likelihood of a therapeutically desirable response, the neoepitopes can be further filtered. Of course, it should be appreciated that downstream analysis need not take into account silent mutations for the purpose of the methods presented herein. However, preferred mutation analyses will provide in addition to the type of mutation (e.g., deletion, insertion, transversion, transition, translocation) also information of the impact of the mutation (e.g., non-sense, missense, etc.) and may as such serve as a first content filter through which silent mutations are eliminated. For example, neoepitopes can be selected for further consideration where the mutation is a frame-shift, non-sense, and/or missense mutation.

In a further filtering approach, neoepitopes may also be subject to detailed analysis for sub-cellular location parameters. For example, neoepitope sequences may be selected for further consideration if the neoepitopes are identified as having a membrane associated location (e.g., are located at the outside of a cell membrane of a cell) and/or if an in silico structural calculation confirms that the neoepitope is likely to be solvent exposed, or presents a structurally stable epitope (e.g., *J Exp Med* 2014), etc.

With respect to filtering neoepitopes, it is generally contemplated that neoepitopes are especially suitable for use herein where omics (or other) analysis reveals that the neoepitope is actually expressed. Identification of expression and expression level of a neoepitope can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, at least 30%, at least 40%, or at least 50% of expression level of the corresponding matched normal sequence, thus ensuring that the (neo) epitope is at least potentially 'visible' to the immune system. Consequently, it is generally preferred that the omics analysis also includes an analysis of gene expression (transcriptomic analysis) to so help identify the level of expression for the gene with a mutation.

There are numerous methods of transcriptomic analysis known in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis, especially including RNAseq. In other aspects, RNA quantification and sequencing is performed using RNA-seq, qPCR and/or rtPCR based methods, although various alternative methods (e.g., solid phase hybridization-based methods) are also deemed suitable.

Viewed from another perspective, transcriptomic analysis may be suitable (alone or in combination with genomic analysis) to identify and quantify genes having a cancer- and patient-specific mutation.

Similarly, proteomics analysis can be performed in numerous manners to ascertain actual translation of the RNA of the neoepitope, and all known manners of proteomics analysis are contemplated herein. However, particularly preferred proteomics methods include antibody-based methods and mass spectroscopic methods. Moreover, it should be noted that the proteomics analysis may not only provide qualitative or quantitative information about the protein per se, but may also include protein activity data where the protein has catalytic or other functional activity. One exemplary technique for conducting proteomic assays is described in U.S. Pat. No. 7,473,532, incorporated by reference herein. Further suitable methods of identification and even quantification of protein expression include various mass spectroscopic analyses (e.g., selective reaction monitoring (SRM), multiple reaction monitoring (MRM), and consecutive reaction monitoring (CRM)). Consequently, it should be appreciated that the above methods will provide patient and tumor specific neoepitopes, which may be further filtered by sub-cellular location of the protein containing the neoepitope (e.g., membrane location), the expression strength (e.g., overexpressed as compared to matched normal of the same patient), etc.

In yet another aspect of filtering, the neoepitopes may be compared against a database that contains known human sequences (e.g., of the patient or a collection of patients) to so avoid use of a human-identical sequence. Moreover, filtering may also include removal of neoepitope sequences that are due to SNPs in the patient where the SNPs are present in both the tumor and the matched normal sequence. For example, dbSNP (The Single Nucleotide Polymorphism Database) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database and other filtering options as described above, the patient and tumor specific neoepitopes may be filtered to remove those known sequences, yielding a sequence set with a plurality of neoepitope sequences having substantially reduced false positives.

Nevertheless, despite filtering, it should be recognized that not all neoepitopes will be visible to the immune system as the neoepitopes also need to be presented on the MHC complex of the patient. Indeed, only a fraction of the neoepitopes will have sufficient affinity for presentation, and the large diversity of MHC complexes will preclude use of most, if not all, common neoepitopes. Consequently, in the context of immune therapy it should thus be readily apparent that neoepitopes will be more likely effective where the neoepitopes are bound to and presented by the MHC complexes. Viewed from another perspective, treatment success with checkpoint inhibitors requires multiple neoepitopes to be presented via the MHC complex in which the neoepitope must have a minimum affinity to the patient's HLA-type. Consequently, it should be appreciated that effective binding and presentation is a combined function of the sequence of the neoepitope and the particular HLA-type of a patient. Most typically, the HLA-type determination includes at least three MHC-I sub-types (e.g., HLA-A, HLA-B, HLA-C) and at least three MHC-II sub-types (e.g., HLA-DP, HLA-DQ, HLA-DR), preferably with each subtype being determined to at least 2-digit depth or at least 4-digit depth. However, greater depth (e.g., 6 digit, 8 digit) is also contemplated herein.

Once the HLA-type of the patient is ascertained (using known chemistry or in silico determination), a structural solution for the HLA-type is calculated or obtained from a database, which is then used in a docking model in silico to determine binding affinity of the (typically filtered) neoepitope to the HLA structural solution. As will be further discussed below, suitable systems for determination of binding affinities include the NetMHC platform (see e.g., Nucleic Acids Res. 2008 Jul. 1; 36(Web Server issue): W509-W512). Neoepitopes with high affinity (e.g., less than 100 nM, less than 75 nM, less than 50 nM) for a previously determined HLA-type are then selected for therapy creation, along with the knowledge of the MHC-I/II subtype.

HLA determination can be performed using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types as is shown in more detail below.

For example, in one preferred method according to the inventive subject matter, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM). Alternatively, the reference sequence may also be built from individual known HLA-alleles based on one or more predetermined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele.

Scoring may further be improved or refined as needed, especially where many of the top hits are similar (e.g., where a significant portion of their score comes from a highly shared set of k-mers). For example, score refinement may include a weighting scheme in which alleles that are substantially similar (e.g., >99%, or other predetermined value) to the current top hit are removed from future consideration. Counts for k-mers used by the current top hit are then re-weighted by a factor (e.g., 0.5), and the scores for each HLA allele are recalculated by summing these weighted counts. This selection process is repeated to find a new top hit. The accuracy of the method can be even further improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA. Further aspects, suitable methods and considerations for high-accuracy in silico HLA typing are described in International PCT/US16/48768, incorporated by reference herein.

Once patient and tumor specific neoepitopes and HLA-type are identified, further computational analysis can be performed by docking neoepitopes to the HLA and determining best binders (e.g., lowest $K_D$, for example, less than 500 nM, or less than 250 nM, or less than 150 nM, or less than 50 nM), for example, using NetMHC. It should be appreciated that such approach will not only identify specific neoepitopes that are genuine to the patient and tumor, but also those neoepitopes that are most likely to be presented on a cell and as such most likely to elicit an immune response with therapeutic effect. Of course, it should also be appreciated that thusly identified HLA-matched neoepitopes can be biochemically validated in vitro prior to inclusion of the nucleic acid encoding the epitope as payload into the virus as is further discussed below.

Of course, it should be appreciated that matching of the patient's HLA-type to the patient- and cancer-specific neoepitope can be done using systems other than NetMHC, and suitable systems include NetMHC II, NetMHCpan, IEDB Analysis Resource (URL immuneepitope.org), RankPep, PREDEP, SVMHC, Epipredict, HLABinding, and others (see e.g., *J Immunol Methods* 2011; 374:1-4). In calculating the highest affinity, it should be noted that the collection of neoepitope sequences in which the position of the altered amino acid is moved (supra) can be used. Alternatively, or additionally, modifications to the neoepitopes may be implemented by adding N- and/or C-terminal modifications to further increase binding of the expressed neoepitope to the patient's HLA-type. Thus, neoepitopes may be native as identified or further modified to better match a particular HLA-type. Moreover, where desired, binding of corresponding wildtype sequences (i.e., neoepitope sequence without amino acid change) can be calculated to ensure high differential affinities. For example, especially preferred high differential affinities in MHC binding between the neoepitope and its corresponding wildtype sequence are at least 2-fold, at least 5-fold, at least 10-fold, at least 100-fold, at least 500-fold, at least 1000-fold, etc.).

Once the desired level of filtering for the neoepitope is accomplished (e.g., neoepitope filtered by tumor versus normal, and/or expression level, and/or sub-cellular location, and/or patient specific HLA-match, and/or known variants), a further filtering step is contemplated that takes into account the gene type that is affected by the neoepitope. For example, suitable gene types include cancer driver genes, genes associated with regulation of cell division, genes associated with apoptosis, and genes associated with signal transduction. However, in especially preferred aspects, cancer driver genes are particularly preferred (which may span by function a variety of gene types, including receptor genes, signal transduction genes, transcription regulator genes, etc.). In further contemplated aspects, suitable gene types may also be known passenger genes and genes involved in metabolism.

As already noted before, it is contemplated that targeting a cancer driver gene is thought to provide an enhanced therapeutic effect as an immune response against a protein encoded by a cancer driver will not only promote a cell-based cytotoxic effect against tumor cells, but also facilitate functional interference with the protein encoded by the cancer driver gene that has the cancer driver neoepitope. Viewed from another perspective, the therapeutic response using systems and methods contemplated herein will target a cancer cell in both, an immune therapeutic approach and a more traditional protein function-based approach. Thus, it is contemplated that filtered neoepitopes are further analyzed to determine their association with a particular gene (e.g., filtered neoepitope is present in an exon of a transcribed gene or present in a mRNA), and that the gene is then identified as belonging to a desired gene type, and especially as being a cancer driver gene. For example, neoepitopes present in a cancer driver gene are identified cancer driver neoepitopes.

With respect to the identification or other determination (e.g., prediction) of a gene as being a cancer driver gene, various methods and prediction algorithms are known in the art, and are deemed suitable for use herein. For example, suitable algorithms include MutsigCV (*Nature* 2014, 505 (7484):495-501), ActiveDriver (*Mol Syst Biol* 2013, 9:637), MuSiC (*Genome Res* 2012, 22(8):1589-1598), OncodriveClust (*Bioinformatics* 2013, 29(18):2238-2244), OncodriveFM (*Nucleic Acids Res* 2012,40(21): e169), OncodriveFML (*Genome Biol* 2016, 17(1):128), Tumor Suppressor and Oncogenes (TUSON) (*Cell* 2013, 155(4): 948-962), 20/20+, and oncodriveROLE (*Bioinformatics* (2014) 30 (17): i549-i555).

Cancer driver genes can also be identified using probabilistic pathway analysis tools, and especially preferred tools include PARADIGM (*Bioinformatics,* 2010, vol. 26 (pg. i237-i245)). PARADIGM assesses the activity of a gene in the context of a genetic pathway diagram φ by drawing inferences from a dataset of observations D. The pathway diagram φ describes connections between hidden gene expression variables, their corresponding observational data, and any regulatory inputs and outputs. Variables are connected to each other by factors, which encode probabilistic dependencies constraining mutually connected variables. PARADIGM then uses a belief-propagation algorithm on a factor graph derived from φ to compute inferred pathway levels (IPLs) for each gene, complex, protein family and cellular process by combining gene expression, copy number and genetic interactions. Positive IPLs reflect how much more likely the gene is active in a tumor (and as such may be a cancer driver gene), and negative IPLs how likely the gene is inactive in the tumor relative to normal. Such methods can be further refined by calculating a Shift (PARADIGM-SHIFT) score that is based on the intuition of comparing the observed downstream consequences of a gene's activity to what is expected from its regulatory inputs as is described elsewhere (*Bioinformatics* (2012) 28 (18): i640-i646).

Alternatively, or additionally, identification of cancer driver genes may also employ various sources for known cancer driver genes and their association with specific cancers. For example, the Intogen Catalog of driver mutations (2016.5) contains the results of the driver analysis performed by the Cancer Genome Interpreter across 6,792 exomes of a pan-cancer cohort of 28 tumor types. Validated oncogenic mutations are identified according to the state-of-the-art clinical and experimental data, whereas the effect of the mutations of unknown significance is predicted by the OncodriveMUT method. Similarly, the Intogen Cancer Drivers Database (2014.12) contains information on the genes identified as drivers in Rubio-Perez and Tamborero et al. (*Cancer Cell* 27 (2015), pp. 382-396).

Moreover, Table 1 below provides exemplary selection for the most common cancer driver genes and their role in particular cancers.

TABLE 1

| Gene symbol | Tumor type |
| --- | --- |
| AURKA | COREAD |
| BAP1 | BRCA |
| BAP1 | BRCA |
| BAP1 | LGG |
| BRCA1 | BRCA |
| BRCA2 | BRCA |
| CCND2 | COREAD |
| CCND2 | GBM |
| CCND3 | COREAD |
| CCNE1 | BLCA |
| CCNE1 | BRCA |
| CCNE1 | OV |
| CCNE1 | UCEC |
| CDK4 | GBM |
| CDK4 | LGG |
| CDK4 | LUAD |
| CDK4 | CM |
| CDK4 | CM |
| CDK6 | GBM |

TABLE 1-continued

| Gene symbol | Tumor type |
| --- | --- |
| CDK6 | LUSC |
| CDKN1B | BRCA |
| CDKN1B | BRCA |
| CDKN1B | PRAD |
| CDKN1B | PRAD |
| CDKN2A | BLCA |
| CDKN2A | BLCA |
| CDKN2A | BRCA |
| CDKN2A | GBM |
| CDKN2A | HNSC |
| CDKN2A | HNSC |
| CDKN2A | RCCC |
| CDKN2A | LGG |
| CDKN2A | LUAD |
| CDKN2A | LUAD |
| CDKN2A | LUSC |
| CDKN2A | LUSC |
| CDKN2A | CM |
| CDKN2A | CM |
| CDKN2B | BLCA |
| CDKN2B | BRCA |
| CDKN2B | GBM |
| CDKN2B | RCCC |
| EGFR | BLCA |
| EGFR | BRCA |
| EGFR | GBM |
| EGFR | HNSC |
| EGFR | HNSC |
| EGFR | LGG |
| EGFR | LGG |
| EGFR | LUAD |
| EGFR | LUAD |
| EGFR | LUSC |
| EGFR | LUSC |
| ERBB2 | BLCA |
| ERBB2 | BRCA |
| ERBB2 | BRCA |
| ERBB2 | COREAD |
| ERBB2 | UCEC |
| FBXW7 | BLCA |
| FBXW7 | HNSC |
| FBXW7 | LUSC |
| FGFR1 | HNSC |
| FGFR2 | STAD |
| FGFR3 | BLCA |
| FGFR3 | BLCA |
| FGFR3 | GBM |
| FGFR3 | UCEC |
| IGF1R | BRCA |
| IGF1R | OV |
| MDM2 | BLCA |
| MDM2 | GBM |
| MDM2 | HNSC |
| MDM2 | LUAD |
| MDM2 | CM |
| MDM4 | GBM |
| MDM4 | LGG |
| MET | GBM |
| MET | GBM |
| MET | RCCC |
| MET | LUAD |
| MET | STAD |
| NF1 | BRCA |
| NF1 | AML |
| NF1 | AML |
| NF1 | OV |
| NF1 | OV |
| NF1 | UCEC |
| NF2 | CM |
| NF2 | UCEC |
| PTEN | BRCA |
| PTEN | BRCA |
| PTEN | COREAD |
| PTEN | COREAD |
| PTEN | GBM |
| PTEN | GBM |
| PTEN | HNSC |
| PTEN | RCCC |

TABLE 1-continued

| Gene symbol | Tumor type |
| --- | --- |
| PTEN | LUSC |
| PTEN | LUSC |
| PTEN | OV |
| PTEN | PRAD |
| PTEN | PRAD |
| PTEN | CM |
| PTEN | CM |
| PTEN | STAD |
| PTEN | THCA |
| PTEN | UCEC |
| PTEN | UCEC |
| SMARCA4 | BRCA |
| SMARCB1 | PRAD |
| STK11 | BRCA |
| STK11 | HNSC |
| STK11 | LUSC |
| STK11 | LUSC |
| STK11 | OV |
| TP53 | BRCA |
| TP53 | AML |
| TP53 | PRAD |
| TP53 | PRAD |
| TP53 | THCA |

Further exemplary cancer driver genes for particular cancers and suitable for use in conjunction with the teachings presented herein include the following:

ALL (acute lymphocytic leukemia) driver genes include CNOT1, CNOT3, FBXW7, FLT3, KRAS, NF1, NRAS, PTEN, RB1, RPL5, SH2B3, and TP53.

AML (acute myeloid leukemia) driver genes include ASXL1, BCOR, CBFB, CEBPA, CHD4, CUL1, DIS3, DNMT3A, EGFR, EZH2, FLT3, IDH1, IDH2, KDM6A, KIT, KRAS, MED12, NF1, NPM1, NRAS, PHF6, PRPF8, PTPN11, RAD21, RUNX1, STAG2, SUZ12, TET2, THRAP3, TP53, U2AF1, and WT1.

BLCA (bladder cancer) driver genes include ACSL6, ACTB, ACTG1, ADAM10, AFF4, AHNAK, AHR, ANK3, APC, AQR, ARFGAP1, ARFGEF2, ARHGAP26, ARHGAP35, ARID1A, ARID1B, ATR, BAP1, BCLAF1, BCOR, BLM, BMPR2, BRAF, BRCA1, CAD, CARM1, CASP8, CAST, CAT, CCAR1, CCT5, CDH1, CDK12, CDKN1A, CDKN1B, CDKN2A, CEP290, CHD3, CHD9, CHEK2, CIC, CLASP2, CLSPN, CLTC, CNOT1, COPS2, CSDE1, CTCF, CTNNB1, CUL2, DDX3X, DDX5, DICER1, DIS3, DLG1, EEF1B2, EIF2AK3, EIF4A2, EIF4G1, ELF1, ELF3, EP300, ERBB2IP, ERBB3, ERCC2, FAM123B, FAT1, FBXW7, FGFR2, FGFR3, FKBP5, FLT3, FN1, FUS, G3BP2, GNAS, GOLGA5, GPS2, HLA-A, HNRPDL, HRAS, HSP90AA1, HSP90AB1, HSPA8, IDH1, IREB2, IRS2, KDM6A, KEAP1, KLF6, LIMA1, MAP3K1, MAP3K4, MAP4K3, MECOM, MED12, MED24, MET, MGA, MLH1, MLL2, MLL3, MTOR, MYH10, MYH11, NAP1L1, NCF2, NCOR2, NDRG1, NFE2L2, NOTCH1, NRAS, NUP107, NUP98, PCDH18, PCSK6, PHF6, PIK3CB, PIP5K1A, PTEN, PTPRU, RAD21, RASA1, RB1, RBM5, RHOA, RPSAP58, SETD2, SETDB1, SF3A3, SF3B1, SFPQ, SMAD4, SMC1A, SOS1, SOS2, STAG1, STAG2, STK4, SUZ12, TAF1, TAOK1, TAOK2, TBL1XR1, TBX3, TGFBR2, THRAP3, TNPO1, TP53, TP53BP1, TRIO, TSC1, TXNIP, ZFP36L2, ZMYM2, and ZNF814.

BRCA (breast cancer) driver genes include ACO1, ACSL6, ACTB, ACVR1B, AFF4, AHNAK, AKAP9, AKT1, ANK3, APC, AQR, ARFGEF2, ARHGAP35, ARID1A, ARID2, ARID4B, ARNTL, ASH1L, ASPM, ATF1, ATIC, ATM, ATR, BAP1, BCOR, BMPR2, BNC2, BPTF, BRAF, BRCA1, BRCA2, CAD, CARM1, CASP8, CAST, CBFB, CCAR1, CCT5, CDH1, CDK12, CDKN1B, CEP290, CHD4, CHD9, CHEK2, CIC, CLASP2, CLSPN, CLTC, CNOT3, CSDE1, CSNK1G3, CTCF, CUL1, DDX3X, DDX5, DHX15, DIS3, EGFR, EIF1AX, EIF2C3, EIF4A2, EIF4G1, ELF1, EP300, ERBB2, ERBB2IP, ERCC2, FBXW7, FLT3, FMR1, FN1, FOXA1, FOXP1, FUBP1, FUS, G3BP2, GATA3, GOLGA5, GPS2, HCFC1, HLA-A, HLF, HNRPDL, HSPA8, IDH1, ITSN1, KALRN, KDM5C, KEAP1, KLF4, KRAS, LCP1, LPHN2, LRP6, MACF1, MAP2K4, MAP3K1, MAX, MECOM, MED12, MED23, MED24, MGA, MKL1, MLH1, MLL, MLL2, MLL3, MLLT4, MSR1, MTOR, MUC20, MYB, MYH11, MYH14, MYH9, NCOR1, NDRG1, NF1, NF2, NOTCH1, NOTCH2, NR4A2, NRAS, NSD1, NUP107, NUP98, PAX5, PBRM1, PCDH18, PCSK6, PHF6, PIK3CA, PIK3CB, PIK3R1, PIK3R3, PIP5K1A, POLR2B, PRKAR1A, PRKCZ, PTEN, PTGS1, PTPRU, RB1, RBBP7, RBM5, RFC4, RHEB, RPGR, RPL5, RUNX1, SEC24D, SETD2, SETDB1, SF3B1, SFPQ, SMAD4, SMARCA4, SOS1, SOS2, SPTAN1, SRGAP1, STAG1, STAG2, STIP1, STK11, STK4, SUZ12, SVEP1, TAF1, TBL1XR1, TBX3, TCF12, TCF7L2, TFDP1, TGFBR2, THRAP3, TNPO1, TOM1, TP53, TRIO, ZFP36L1, and ZFP36L2.

CLL (chronic lymphocytic leukemia) driver genes include ACTG1, ANK3, ARID1A, ATM, BCOR, CLSPN, CNOT3, CREBBP, DDX3X, EGFR, EP300, ERBB2IP, FBXW7, FGFR2, FGFR3, HNRPDL, IDH1, IRF2, KDM6A, KRAS, MED12, MLL, MLL2, MLL3, MTOR, MYD88, NCOR1, NF1, NOTCH1, NRAS, PBRM1, PLCB1, RB1, SETDB1, SF3B1, STAG2, TP53, and XPO1.

CM (cutaneous melanoma) driver genes include ACO1, ACSL3, ACTG1, ACTG2, ACVR1B, ACVR2A, AFN4, AHCTF1, AHNAK, AHR, AKT1, ANK3, AQR, ARFGAP1, ARFGEF2, ARHGAP26, ARHGAP29, ARHGAP35, ARHGEF2, ARHGEF6, ARID1B, ARID2, ASPM, ATF1, ATIC, ATP6AP2, ATRX, B2M, BAP1, BAZ2B, BCLAF1, BLM, BMPR2, BNC2, BPTF, BRAF, BRCA1, BRWD1, C15orf55, CASP1, CASP8, CAST, CAT, CBFB, CCAR1, CCT5, CDC73, CDH1, CDK4, CDKN1A, CDKN2A, CEP290, CHD1L, CHD3, CHD6, CHD9, CHEK2, CIC, CLASP2, CLCC1, CLOCK, CLSPN, CLTC, CNOT3, COL1A1, COPS2, CRTC3, CSDA, CSNK1G3, CTCF, CTNNB1, CUL1, CUL2, CUL3, CYLD, CYTH4, DDX3X, DDX5, DHX15, DICER1, DIS3, DLG1, DNMT3A, EIF1AX, EIF2AK3, EIF4A2, EIF4G1, EIF4G3, ELF1, ELF3, EP300, ERBB2IP, ERBB3, EZH2, FAF1, FANCI, FAS, FBXW7, FCRL4, FGFR3, FMR1, FN1, FOXP1, FUBP1, FXR1, G3BP2, GATA3, GNG2, GOLGA5, HDAC3, HDAC9, HLA-A, HLA-B, HLF, HNRPDL, HRAS, HSPA8, IDH1, IDH2, IREB2, IRF7, ITGA9, ITSN1, JMY, KDM5C, KDM6A, KLF4, KLF6, KRAS, LCP1, LDHA, LNPEP, LRP6, LRPPRC, MAGI2, MAP2K1, MAP2K4, MAP3K1, MAP3K11, MAP3K4, MAP4K3, MAT2A, MCM3, MCM8, MECOM, MED17, MED24, MEN1, MFNG, MKL1, MLH1, MLL3, MSR1, NCF2, NCKAP1, NCOR1, NDRG1, NF1, NF2, NFATC4, NFE2L2, NOTCH1, NPM1, NR2F2, NR4A2, NRAS, NTN4, NUP107, NUP98, PAX5, PCDH18, PERI, PHF6, PIK3C2B, PIK3CA, PIK3CB, PIK3R1, PIK3R3, PIP5K1A, PLCB1, POLR2B, POM121, PPP2R1A, PPP2R5A, PPP2R5C, PPP6C, PPP6C, PRRX1, PSMA6, PTEN, PTGS1, RAC1, RAD21, RAD23B, RASA1, RASA2, RB1, RBBP7, RGS3, RHEB, RHOA, RHOT1, RPL22, RPL5, RTN4, RUNX1, SEC24D, SETDB1, SF3A3, SF3B1, SFPQ, SMAD2, SMAD4, SMC1A, SMURF2, SOS1, SOS2, SOX9, SPOP, STAG1, STAG2, STK11, SUZ12, SVEP1, SYK, SYNCRIP, TAOK1, TBX3, TCF12, TCF4, TFDP1, TFDP2, TGFBR2, TJP2, TNPO1, TP53, TRERF1, USP6, VHL, VIM, WASF3, WIPF1, WNK1, WT1, XRN1, YBX1, ZC3H11A, ZFP36L2, ZMYM2, ZNF638, and ZNF814.

COREAD (colorectal adenocarcinoma) driver genes include ACO1, ACSL6, ACVR1B, AKAP9, APC, ARID1A, ARNTL, ASPM, ATM, ATRX, AXIN2, BCOR, BMPR2, BPTF, BRAF, BRWD1, CAD, CASP8, CDC73, CDK12, CDKN1B, CEP290, CHD4, CHD9, CLSPN, CNOT1, CREBBP, CTCF, CTNNB1, CUL1, DIS3, DNMT3A, EGFR, ELF3, FAM123B, FBXW7, FN1, FOXP1, FXR1, GATA3, GNAS, GOLGA5, IDH2, ITSN1, KRAS, LPHN2, MAP2K1, MAP3K4, MECOM, MED12, MED24, MGA, MLL2, MSR1, MYH10, NF1, NR2F2, NR4A2, NRAS, NTN4, NUP107, NUP98, PCBP1, PIK3CA, PIK3R1, POLR2B, PPP2R1A, PTEN, PTGS1, PTPN11, PTPRU, RAD21, RBM10, RTN4, RUNX1, SF3B1, SMAD2, SMAD4, SMC1A, SOS2, SOX9, SRGAP3, STAG2, SYNCRIP, TAF1, TBX3, TCF12, TCF7L2, TGFBR2, TP53, TP53BP1, TRIO, WIPF1, WT1, and ZC3H11A.

DLBC (diffuse large B cell lymphoma) driver genes include ACTB, AKAP9, ARID1A, CHD4, CREBBP, FBXO11, MLL2, MYC, SMARCA4, and TP53.

ESCA (esophageal cancer) driver genes include ACO1, ACSL6, ACVR1B, ADAM10, AFF4, AHR, ARFGEF2, ARHGAP26, ARHGAP35, ARID1A, ARID2, ARNTL, ASPM, ATM, ATR, ATRX, BAP1, BCLAF1, BLM, BPTF, CAPN7, CDH1, CDKN1B, CDKN2A, CEP290, CHD4, CIC, CLTC, CNOT1, CNOT3, CREBBP, CSNK1G3, CTNNB1, CUL3, DDX5, DLG1, EEF1A1, EGFR, EIF2AK3, EIF4G1, ELF3, EP300, ERBB2IP, ERCC2, EZH2, FBXW7, FGFR2, FLT3, HGF, HLA-B, IREB2, IRS2, ITSN1, KALRN, KDM6A, LRP6, MACF1, MAP2K4, MAP3K4, MED12, MET, MGA, MLL2, MSR1, MTOR, NCKAP1, NFE2L2, NSD1, NUP107, NUP98, PAX5, PIK3CA, PTPRU, RAD21, RBM10, RHOA, RTN4, SETD2, SF3B1, SHMT1, SMAD4, SMARCA4, SMC1A, SOX9, SPTAN1, SRGAP3, SYNCRIP, TAF1, TAOK1, TAOK2, TBX3, TP53, TP53BP1, TRIO, WT1, ZC3H11A, ZFP36L2, and ZNF814.

GBM (glioblastoma multiforme) driver genes include ACAD8, ADAM10, AKAP9, ANK3, AQR, ARFGEF2, ARHGAP35, ARHGEF6, ARID1A, ARID2, ATRX, BAP1, BPTF, BRAF, BRCA1, CAD, CARM1, CASP1, CHD8, CLOCK, CLTC, CNOT1, CSDE1, CUL1, DIS3, EGFR, EZH2, FAT1, FN1, HDAC9, HSP90AB1, IDH1, KALRN, KDM5C, KDM6A, KDR, KRAS, LRP6, MAP3K4, MAP4K3, MAX, MEN1, MET, MLL, NCF2, NCOR1, NEDD4L, NF1, NFATC4, NR2F2, NUP107, PAX5, PBRM1, PCDH18, PIK3CA, PIK3CB, PIK3R1, PRPF8, PTEN, PTPN11, RB1, RPL5, RPSAP58, SF3B1, SIN3A, SOS1, SOX9, SPTAN1, STAG2, TGFBR2, TJP1, TP53, TRIO, WT1, and ZNF814.

HC (hepatocarinoma) driver genes include ACVR2A, APC, ARHGAP35, ARID1A, ARID1B, ARID2, ASH1L, ATRX, BLM, BPTF, CEP290, CNOT1, CTNNB1, FLT3, IDH1, ITSN1, MACF1, MLL3, MYH10, NF1, NFATC4, NFE2L2, PBRM1, PIK3CA, PTEN, RTN4, SETDB1, SF3B1, TBL1XR1, and TP53.

HNSC (head and neck squamous cell carcinoma) driver genes include ACAD8, ACTB, ACTG1, ACVR2A, ADAM10, AHR, AKT1, APAF1, APC, ARFGAP1, ARFGEF2, ARHGAP35, ARHGEF6, ARID1B, ARID2, ATIC, ATM, ATP6AP2, ATR, ATRX, B2M, BAP1, BAZ2B, BCL11A, BMPR2, BNC2, BPTF, BRAF, BRCA1, BRWD1, CAD, CARM1, CASP1, CASP8, CAT, CCAR1, CCT5, CDH1, CDK12, CDKN1B, CDKN2A, CEP290, CHD9, CIITA, CLASP2, CLSPN, CNOT4, COL1A1, CSNK2A1, CTCF, CTNNB1, CUL1, CUL3, CYLD, DDX3X, DICER1, DNMT3A, EEF1A1, EGFR, EIF2C3, ELF1, ELF4, EP300, EPHA2, EZH2, FAT1, FAT2, FBXW7, FGFR2, FLT3, FMR1, FN1, FOXP1, FUBP1, G3BP2, GNAS, GPSM2, HLA-A, HLA-B, HNRPDL, HRAS, HSPA8, IREB2, IRF6, IRS2, KALRN, KDM5C, KDM6A, KLF6, LAMA2, LPHN2, MACF1, MAP3K1, MAP4K3, MED17, MEF2C, MEN1, MGA, MGMT, MLL, MLL2, MSR1, MTOR, MUC20, MYH9, NCF2, NCKAP1, NCOR1, NEDD4L, NF1, NFATC4, NFE2L2, NOTCH1, NOTCH2, NR4A2, NSD1, NUP107, PABPC3, PAX5, PBRM1, PCDH18, PIK3CA, PIK3R1, PIK3R3, POLR2B, PPP2R1A, PPP2R5C, PRPF8, PRRX1, PSIP1, RAC1, RAD21, RASA1, RASGRP1, RHOA, RPL22, RPSAP58, RUNX1, SEC24D, SF3B1, SIN3A, SMAD2, SMARCA4, SMC1A, SOX9, SPOP, SPTAN1, STAG2, STIP1, TAOK1, TAOK2, TBL1XR1, TBX3, TCF12, TCF4, TFDP1, TFDP2, TGFBR2, THRAP3, TJP2, TP53, TRIO, TRIP10, U2AF1, WHSC1, ZC3H11A, and ZNF750.

LGG (low-grade glioma) driver genes include ACO1, ARFGEF2, ARHGAP26, ARHGEF6, ARID1A, ARID1B, ARID2, ATRX, CAD, CDK12, CHEK2, CIC, DDX3X, EEF1B2, EGFR, EIF1AX, FAM123B, FAT1, FUBP1, HGF, IDH1, IDH2, KAT6B, MAX, MECOM, MET, MLL, MLL2, MTOR, NCOR1, NEDD4L, NF1, NF2, NOTCH1, PIK3CA, PIK3R1, PTEN, PTPN11, RASA1, RB1, SETD2, SMARCA4, TAF1, TCF12, TJP1, TP53, TRIO, ZMYM2, ZNF292, and ZNF814.

LUAD (lung adenocarcinoma) driver genes include ACAD8, ACO1, ACTG1, ACTG2, ACVR1B, ACVR2A, ADAM10, AFF4, AKT1, ARFGAP1, ARHGAP26, ARID1A, ATIC, ATP6AP2, BAP1, BAZ2B, BLM, BMPR2, BRAF, BRWD1, CAPN7, CARM1, CASP8, CAT, CCAR1, CCT5, CDH1, CDK12, CDKN1B, CDKN2A, CHD1L, CHEK2, CIC, CLASP2, CLSPN, CNOT3, CNOT4, COL1A1, COPS2, CREBBP, CRNKL1, CSNK1G3, CTCF, CTNNB1, CUL2, CUL3, CYLD, DDX3X, DDX5, DHX15, DNMT3A, EEF1B2, EFTUD2, EGFR, EIF2AK3, EIF2C3, EIF4A2, EIF4G1, EP300, EPHA4, EPHB2, ERBB2IP, ERCC2, EZH2, FAT1, FBXW7, FGFR2, FMR1, FN1, FUBP1, FXR1, G3BP1, G3BP2, GNAI1, GNG2, GPSM2, HLA-A, HSP90AA1, HSP90AB1, HSPA8, IDH1, IREB2, IRS2, KDM6A, KDR, KEAP1, KLF6, KRAS, LCP1, LDHA, LPHN2, MAP2K1, MAP2K4, MAP3K1, MAP3K4, MAP4K1, MAP4K3, MAX, MED17, MED24, MEN1, MET, MGA, MKL1, MLH1, MLL, MLL3, MMP2, MSR1, MYB, MYH10, NCK1, NCKAP1, NEDD4L, NF1, NF2, NFE2L2, NPM1, NRAS, NTN4, NTRK2, NUP107, NUP98, PAX5, PBRM1, PCSK6, PHF6, PIK3R1, PIK3R3, PIP5K1A, POLR2B, PPP2R1A, PPP2R5A, PRPF8, PRRX1, PSMA6, PSMD11, PTEN, PTGS1, PTPN11, RAD23B, RASA1, RB1, RBM10, RBM5, RHEB, RTN4, SETD2, SETDB1, SF3B1, SFPQ, SHMT1, SIN3A, SMAD2, SMAD4, SMARCA4, SMC1A, SOX9, SPRR3, STAG1, STIP1, STK11, STK4, SVEP1, SYNCRIP, TAOK1, TAOK2, TBL1XR1, TCF12, TCF4, TCF7L2, TFDP1, TGFBR2, TNPO1, TOM1, TP53, TP53BP1, U2AF1, UPF3B, ZMYM2, and ZNF814.

LUSC (lung small cell carcinoma) driver genes include ABL2, ACAD8, ACO1, ACSL6, ACTG2, ACVR1B, ADAM10, AFF4, AQR, ARFGEF2, ARHGEF6, ARID1A, ARID1B, ARNTL, B2M, BLM, CASP8, CAST, CCAR1, CDC73, CDH1, CDKN1A, CDKN2A, CHD1L, CHD3, CHEK2, CIC, CLASP2, CLOCK, CNOT3, CNOT4, COPS2, CSDA, CSDE1, CTNNB1, CTTN, CUL1, DDX3X, DHX15, DHX9, DLG1, EEF1A1, EGFR, EIF2C3, EIF4A2, ELF1, ERBB2IP, EZH2, FGFR2, FGFR3, FMR1, FN1, FOXP1, FUBP1, FXR1, G3BP2, GATA3, GNAI1, GOLGA5, GPSM2, HLA-A, HLF, HRAS, HSP90AA1, HSP90AB1, HSPA8, IDH1, IREB2, IRS2, ITSN1, KDM5C, KEAP1, KRAS, MAP2K1, MAP3K1, MAP3K4, MED17, MED24, MEN1, MET, MKL1, MLH1, MLL, MLL2, MUC20, MYB, NCF2, NCK1, NDRG1, NF1, NFATC4, NFE2L2, NOTCH1, NR4A2, NTN4, NUP107, NUP98, PAX5, PCDH18, PCSK6, PHF6, PIK3CA, PIK3CB, PIK3R3, PIP5K1A, PPP2R5C, PRPF8, PTEN, PTPN11, RAD21, RASA1, RB1, RBM10, RGS3, RPL5, RTN4, SEC24D, SETD2, SETDB1, SF3A3, SF3B1, SIN3A, SMAD2, SMAD4, SPTAN1, SRGAP3, STAG1, STK11, STK4, SUZ12, SYNCRIP, TAOK2, TBL1XR1, TBX3, TFDP1, TFDP2, TGFBR2, THRAP3, TJP2, TNPO1, TOM1, TP53, UPF3B, WIPF1, WT1, ZC3H11A, and ZFP36L2.

MB (medulloblastoma) driver genes include ARID1A, ARID1B, ARID2, BCLAF1, BCOR, CCAR1, CREBBP, CTNNB1, DDX3X, FBXW7, FMR1, KDM6A, MGA, MLL2, MLL3, NF1, PIK3CA, PRKAR1A, PTCH1, SMARCA4, SMO, TAF1, TCF4, and TP53.

MM (multiple myeloma) driver genes include APC, ARHGAP35, ARID2, BRAF, CASP8, CEP290, CHD9, DDX3X, FAM46C, FXR1, KRAS, MECOM, NF1, NRAS, NSD1, PIK3CA, SF3B1, and TP53.

NB (neuroblastoma) driver genes include AHR, ALK, ANK3, ARID1A, ATM, ATRX, CEP290, COL1A1, CREBBP, EIF2C3, KLF4, LRP6, MACF1, MECOM, MET, MLL2, MYCN, NF1, NOTCH1, NRAS, PBRM1, PIK3CA, PIK3CB, PTPN11, STAG1, TAF1, and TRIO.

NSCLC (non-small cell lung cancer) driver genes include AKAP9, APC, HGF, KALRN, KEAP1, KRAS, MLL3, RB1, SEC24D, SMARCA4, and TP53.

OV (ovarian cancer) driver genes include ACO1, ACTG1, AFF4, ARID1A, ASH1L, ASPM, ATF1, ATIC, ATR, ATRX, BAP1, BAZ2B, BMPR2, BRAF, BRCA1, BRCA2, CASP1, CCAR1, CCT5, CDK12, CHD1L, CHD4, CLASP2, CLSPN, CSDE1, CTNNB1, CUL2, DDX5, DLG1, DNMT3A, EIF2AK3, EIF4A2, ERBB2IP, F8, FAM123B, FBXW7, FLT3, FMR1, GNAS, GOLGA5, GPS2, HDAC3, HGF, HSP9OAA1, ITSN1, KRAS, LPHN2, MAP3K4, MAP4K3, MECOM, MED12, MKL1, MLH1, MLL2, MYH10, NCKAP1, NDRG1, NF1, NOTCH1, NR4A2, NRAS, NSD1, PIK3CA, POLR2B, PTEN, RB1, RHOA, SETD2, SETDB1, SIN3A, SOS1, STAG1, STAG2, TBX3, TCF7L2, TFDP1, TGFBR2, TJP1, TOM1, TP53, TP53BP1, TRIO, and YBX1.

PAAD (pancreas adenocarcinoma) driver genes include ACVR1B, AHNAK, ANK3, ARHGAP35, ARID1A, ARID2, ATM, CREBBP, EP300, EPC1, KRAS, MAP2K4, MLL3, PBRM1, PCDH18, PCSK6, SF3B1, SMAD4, SMARCA4, TGFBR2, and TP53.

PRAD (prostate adenocarcinoma) driver genes include ADCY1, AHNAK, AKAP9, APC, AQR, ARFGAP3, ARID1B, ATIC, ATM, ATRX, BCLAF1, BCOR, BNC2, BPTF, BRAF, CASP1, CAT, CDC27, CDH1, CDKN1B, CEP290, CHD1L, CHD3, CHD4, CHEK2, CNOT1, CNOT3, CNTNAP1, CTNNB1, CUL2, CUL3, EEF1B2, EGFR, EIF2AK3, EIF4G1, EP300, ERCC2, FAT1, FGFR2, FIP1L1, FN1, FRG1, G3BP2, GNAS, HGF, HNF1A, HRAS, HSP90AB1, HSPA8, IDH1, IRS2, KDM6A, KEAP1, MECOM, MED12, MLL2, MYH10, NAP1L1, NKX3-1, NOTCH1, NOTCH2, NUP98, PCDH18, PIK3CB, PLXNA1, PRPF8, PTEN, RPSAP58, SCAI, SETDB1, SMAD4, SMARCA1, SMARCB1, SPOP, SVEP1, TAOK2, TBL1XR1, TBX3, THRAP3, TJP1, TJP2, TP53, TP53BP1, TRIO, WHSC1L1, WNT5A, ZFHX3, and ZNF814.

RCCC (renal clear cell carcinoma) driver genes include ACO1, ACTG1, AHR, AKT1, ARHGAP26, ARID1A, ARID1B, ARID2, ASH1L, ATF1, ATM, BAP1, BCLAF1, BCOR, BMPR2, CAD, CAT, CCAR1, CDC73, CDH1, CHEK2, CLTC, CNOT3, CNOT4, COPS2, CSDA, CTCF, CUL1, DDX3X, DDX5, DHX15, DICER1, DIS3, EEF1A1, EGFR, EIF2AK3, EIF2C3, EIF4A2, EIF4G1, ELF1, ERBB2IP, EZH2, FAM123B, FLT3, FMR1, FUS, G3BP2, HDAC9, HLF, HNRPDL, HSP90AB1, IDH1, ITSN1, KDM5C, KDM6A, KEAP1, LCP1, LPHN2, LRP6, MAX, MED17, MED24, MET, MGA, MKL1, MLL3, MTOR, NCOR1, NFE2L2, NTN4, NUP98, PABPC1, PBRM1, PCDH18, PCSK6, PHF6, PIK3R1, PIP5K1A, PPP2R1A, PSMA6, PSME3, PTEN, RASA1, RPL22, RPL5, SEC24D, SETD2, SHMT1, SIN3A, SMAD2, SMC1A, SOX9, SRGAP3, TAOK2, TBL1XR1, TCF12, TJP1, TJP2, TP53BP1, TRIO, VHL, WHSC1L1, WT1, ZFP36L2, and ZNF814.

SCLC (small cell lung cancer) driver genes include AHNAK, AHR, AKAP9, ANK3, ARID1A, ARID1B, ARID2, ASH1L, ASPM, ATR, ATRX, BAZ2B, BCLAF1, BMPR2, BNC2, BRWD1, CCT5, CDK12, CHD1L, CHEK2, CLSPN, CREBBP, DICER1, EIF2AK3, EP300, FAM123B, FAT1, FN1, GNAS, HGF, HSP90AB1, ITSN1, KALRN, KDM6A, MED12, MLL, MLL2, MLL3, MNDA, MSR1, MTOR, MYB, NCKAP1, NF1, NOTCH1, NR4A2, NUP107, PIK3CA, PTEN, PTPRU, RAD21, RB1, SIN3A, SOS1, SOS2, SPTAN1, TAF1, TBX3, TJP1, TP53, and ZC3H11A.

STAD (stomach adenocarcinoma) driver genes include ACAD8, ACSL6, ACTG2, ACVR1B, ACVR2A, ADAM10, AFF4, AKAP9, ANK3, APC, AQR, ARFGEF1, ARHGAP26, ARHGAP35, ARHGEF6, ARID1A, ARID1B, ARID4A, ASH1L, ATIC, ATP6AP2, ATR, ATRX, BAP1, BCOR, BPTF, BRAF, BRCA1, CAD, CAPN7, CASP8, CAT, CCAR1, CCT5, CDC73, CDH1, CDKN2A, CEP290, CHD1L, CHD3, CHEK2, CLASP2, CLOCK, CLTC, CNOT1, CNOT4, COL1A1, COPS2, CSDA, CSDE1, CSNK1G3, CTNNB1, CUL1, CUL2, CUL3, CYLD, DDX5, DHX15, DIS3, DLG1, DNMT3A, EEF1A1, EGFR, EIF2AK3, EIF4A2, EIF4G1, ELF3, EPHA1, ERBB2IP, ERCC2, EZH2, FAM123B, FAS, FGFR2, FLT3, FOXP1, FUBP1, G3BP2, GATA3, GNA11, GNAI1, GOLGA5, HDAC3, HLA-A, HLA-B, HNRPDL, HSP90AB1, IREB2, IRF2, IRS2, KDM6A, KLF4, KLF6, KRAS, LCP1, LPHN2, MACF1, MAP2K1, MAP2K4, MAP3K1, MECOM, MED12, MED17, MET, MKL1, MLH1, MSR1, MYH11, MYH9, NAP1L1, NCK1, NCKAP1, NEDD4L, NFE2L2, NR2F2, NR4A2, NSD1, NUP107, NUP98, PCSK5, PHF6, PIK3CA, PIK3CB, PIK3R1, PIP5K1A, POLR2B, PPP2R1A, PRRX1, PTEN, PTGS1, PTPN11, PTPRF, PTPRU, RAD21, RASA1, RBBP7, RBM5, RHOA, RPL22, RTN4, RUNX1, SETD2, SF3B1, SIN3A, SMAD2, SMAD4, SMARCA4, SMC1A, SOS1, SOS2, SOX9, SPOP, SRGAP3, STARD13, STIP1, STK4, SUZ12, TAF1, TAOK2, TBL1XR1, TBX3, TCF4, TCF7L2, TFDP1, THRAP3, TJP1, TJP2, TNPO1, TNPO2, TP53, TP53BP1, WIPF1, WT1, ZC3H11A, and ZMYM2.

THCA (thyroid cancer) driver genes include AHNAK, AKAP9, ARHGAP26, ARID2, BPTF, BRAF, CDK12, CHD3, CTNNB1, DICER1, EIF1AX, GNAS, HNRPDL, HRAS, KRAS, LDHA, MLL, MLL3, NCK1, NRAS, NSD1, PIK3CA, PPM1D, PPP2R1A, PRPF8, PTEN, RPSAP58, TJP1, TP53, TRIO, WIPF1, and ZC3H11A.

UCEC (uterine corpus endometrioid cancer) driver genes include ACACA, ACTB, ACTG1, AHR, AKT1, ALK, ANK3, ARAP3, ARHGAP35, ARHGEF6, ARID1A, ARID5B, ARNTL, ATF1, ATIC, ATM, ATR, AXIN1, BAZ2B, BCLAF1, BMPR2, BRAF, BRCA1, CAPN7, CARM1, CAST, CAT, CCND1, CDKN1B, CHD3, CHD4, CHD9, CHEK2, CLOCK, CLTC, CNOT4, CSNK1G3, CTCF, CTNNB1, CTNND1, CUL1, CUX1, DEPDC1B, DHX15, DHX35, DICER1, DIS3, DNMT3A, EGFR, EIF1AX, EIF2AK3, EIF2C3, EIF4A2, EIF4G1, EP300, ERBB3, FAM123B, FAS, FBXW7, FGFR2, FLT3, FOXA2, FUBP1, FXR1, G3BP2, GNAI1, GPS2, GPSM2, HDAC3, HGF, IDH1, ING1, INPP4A, INPPL1, IREB2, KDM6A, KLF4, KRAS, MAP2K4, MAP3K1, MAX, MED17, MET, MGA, MKL1, MLH1, MLH3, MUC20, MYB, MYH10, NCF2, NCKAP1, NCOR1, NDRG1, NEDD4L, NF2, NFE2L2, NR2F2, NRAS, NUP93, PCDH18, PGR, PHF6, PIK3CA, PIK3R1, PIK3R3, PLCG1, PLXNB2, PPP2R1A, PPP2R5A, PPP2R5C, PRPF8, PRRX1, PTEN, PTPN11, RAD21, RAD23B, RBBP7, RBM5, RHEB, ROBO2, RPL22, RPL5, RTN4, RUNX1, SEC31A, SHMT1, SMAD2, SMC1A, SOX17, SPOP, SRGAP3, STIP1, SUZ12, SYNCRIP, TBL1XR1, TBX3, TFDP1, TGFBR2, TP53, TP53BP1, U2AF1, VHL, WIPF1, ZC3H11A, ZFHX3, ZFP36L2, ZMYM2, and ZNF814.

Upon identification of the filtered neoepitope as a cancer driver neoepitope, one or more immune therapeutic agents may be prepared using the sequence information of the cancer driver neoepitope. Among other agents, it is especially preferred that the patient may be treated with a virus that is genetically modified with a nucleic acid construct that leads to expression of at least one of the identified neoepitopes to initiate an immune response against the tumor. For example, suitable viruses include adenoviruses, adeno-associated viruses, alphaviruses, herpes viruses, lentiviruses, etc. However, adenoviruses are particularly preferred. Moreover, it is further preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol.* 1998 February; 72(2): 926-933). Most typically, the desired nucleic acid sequences (for expression from virus infected cells) are under the control of appropriate regulatory elements well known in the art. Regardless of the type of recombinant virus it is contemplated that the virus may be used to infect patient (or non-patient cells) cells ex vivo or in vivo. For example, the virus may be injected subcutaneously or intravenously to so infect the patients antigen presenting cells. Alternatively, immune competent cells (e.g., NK cells, T cells, macrophages, dendritic cells, etc.) may be infected in vitro and then transfused to the patient. Alternatively, immune therapy need not rely on a virus but may be effected with nucleic acid vaccination, or other recombinant vector that leads to the expression of the neoepitopes (e.g., as single peptides, tandem mini-gene, etc.) in desired cells, and especially immune competent cells.

Likewise, further immunotherapeutic agents other than (viral) expression vectors are also deemed suitable and include genetically engineered cells (and especially various immune competent cells) that express a chimeric antigen receptor having affinity to the cancer driver neoepitope, or a high affinity CD16 receptor having affinity to an antibody that binds specifically to the cancer driver neoepitope. For example, contemplated immunotherapeutic agents include NK cells (e.g., aNK cells, haNK cels, or taNK cells, commercially available from NantKwest, 9920 Jefferson Blvd. Culver City, Calif. 90232) or genetically modified T-cells (e.g., expressing a T-cell receptor) or T-cells stimulated ex vivo with HLA-matched patient- and cancer-specific neoepitopes.

Alternatively, the cancer driver neoepitope(s) may also be administered as peptides, optionally bound to a carrier protein to so act as a cancer vaccine. In further contemplated aspects, the cancer driver neoepitopes may also be used to make antibodies that specifically bind to the cancer driver neoepitope. Such antibodies may be human, humanized, or entirely synthetic antibodies as described in WO 2016/172722.

In addition, it should also be recognized that once the neoepitope is identified as a cancer driver neoepitope, a drug may be selected that targets the protein that is encoded by the cancer driver gene harboring the cancer driver neoepitope. For example, where the cancer driver gene encodes a receptor, receptor antagonists or inhibitors or antibodies against the receptor (or its ligand) may be administered that are specific to the receptor. Similarly, where the cancer driver gene encodes a kinase, a kinase inhibitor may be administered to the patient. Therefore, it should be appreciated that identification of a cancer driver neoepitope may provide a combined treatment option that targets the mutated protein using the immune system and the function of the mutated protein.

Consequently, the inventors also contemplate an immune therapeutic composition that will include a carrier that is coupled to (i) a synthetic antibody having binding specificity to a patient specific cancer driver neoepitope, (ii) a synthetic patient specific cancer driver neoepitope, (iii) a nucleic acid encoding the patient specific cancer driver neoepitope, or (iv) a chimeric antigen receptor having binding specificity to the patient specific cancer driver neoepitope. For example, where the immune therapeutic composition is formulated as a vaccine, the carrier will typically comprises a single carrier protein (e.g., KLH or albumin) or a pharmaceutically acceptable polymer suitable for vaccination. On the other hand, where the immune therapeutic composition is used as a cell or virus based composition, the carrier will typically include an immune competent cell (e.g., CD8+ T cell, a dendritic cell, or a NK cell) or a recombinant virus (e.g., adenovirus) that includes a nucleic acid encoding the cancer driver neoepitope. As is customary in the art, immune therapeutic compositions will generally include a pharmaceutically acceptable carrier suitable for injection or infusion.

EXAMPLES

Data Sets: TCGA WGS and RNAseq data for various cancers as indicated below were downloaded from the University of California, Santa Cruz (UCSC) Cancer Genomics Hub. TCGA samples were selected based on the availability of complete WGS data to aid with in-silico HLA typing. RNAseq data of corresponding samples were used when available.

Identification of tumor variants and neoepitopes: Single nucleotide variants (SNVs) and insertions/deletions (indels) were identified by location-guided synchronous alignment of tumor and normal samples using BAM files in a manner substantially as disclosed in US 2012/0059670A1 and US 2012/0066001A1. Since HLA-A alleles predominantly bind to 9-mer peptide fragments, the inventors focused on the identification of 9-mer neoepitopes. Neoepitopes were identified by creating all possible permutations of 9-mer amino acid strings derived from an identified SNV or indel (i.e., each 9-mer had the changed amino acid in a unique position). As a means to reduce possible off-target effects of a particular neoepitope, the inventors filtered all identified neoepitopes against all possible 9-mer peptide sequences created from every known human gene. In addition, the inventors also filtered for single nucleotide polymorphisms from dbSNP to account for rare protein sequences that may have been missed within the sequencing data. Neoepitopes were further ranked by RNA expression as well as by allele frequency of the observed coding variant to offset issues arising from tumor heterogeneity.

HLA typing: HLA typing data were not available for TCGA samples; therefore, the inventors performed in-silico HLA typing using WGS, RNAseq data, and the HLA forest algorithm substantially as described in PCT/US16/48768. Briefly, the Burrows-Wheeler alignment algorithm was used to align sequencing reads to every different HLA allele within the IMGT/HLA database. Each alignment is given a score based on conservation of bases, with the read quality score taken into account. Each HLA allele will then have a sum of scores accounting for how well each read aligns to a certain HLA allele, and the allele with the highest score is selected as a primary allele typing. Secondary allele typing is then performed by removing reads that perfectly align to the primary allele typing, and subsequent reads are then rescored without alignments to the primary allele. Using this process, the inventors obtained typing results for HLA-A, HLA-B, HLA-C, and HLA-DRB1 for all samples to a level of at least 4 digits.

Neoepitope-HLA affinity determination: NetMHC 3.4 was used to predict whether a neoepitope would bind to a specific HLA allele. To reduce the complexity space, the inventors chose to restrict binding analysis to HLA-A alleles, as they are the most well-characterized HLA alleles and have the best binding affinity models. Because the NetMHC 3.4 tool does not have models for every identified HLA-A allele, a HLA supertype was chosen for binding predictions if the patient's HLA-A typing was not available for use in NetMHC 3.4. Neoepitopes with predicted binding affinities <500 nM protein concentration were retained for further analysis. However, other more stringent binding criteria (<250 nM, or <150 nM, or <50 nM) are also deemed appropriate.

Coding mutation and neoepitope load across cancer types: WGS data and corresponding RNAseq data, when available, were used to establish a baseline of potential neoepitopes and somatic coding variants per megabase of coding DNA for 750 patient samples across 23 cancer classifications as is shown in FIG. 1. Here, neoepitope and variant counts are shown for 750 patient samples across 23 cancer classifications within TCGA. The upper panel illustrates neoepitope counts, while the lower panel illustrates variant counts. The y-axis shows counts per megabase of coding DNA (88 MB for human genome assembly (hg)19). The x-axis shows each cancer classification with the number of patient samples shown in parenthesis. Median sample counts are indicated by squares. The pie chart below indicates the percentage of neoepitopes and normal epitopes (here: found in matched normal tissue or known SNP database) within all cancer types.

As can be readily taken from FIG. 1, mutational and neoepitope loads varied across different cancer types, with melanoma and squamous cell lung cancer having the highest neoepitope load and thyroid cancer and acute myeloid leukemia having the lowest neoepitope load. Filtering of presumptive neoepitopes against a database of known human sequences to remove potential off-target effects revealed that only 10% of identified neoepitopes map to a fragment of a known protein; therefore, most mutations generate a unique protein sequence. However, even though the fraction of unique neoepitopes is relatively high, expression and presentation cannot be presumed to occur. Indeed, as is further shown in more detail below, it should be recognized that the number of expressed and presented neoepitopes is dramatically lower than the number of neoepitopes identified by sequencing only.

Figure 2:
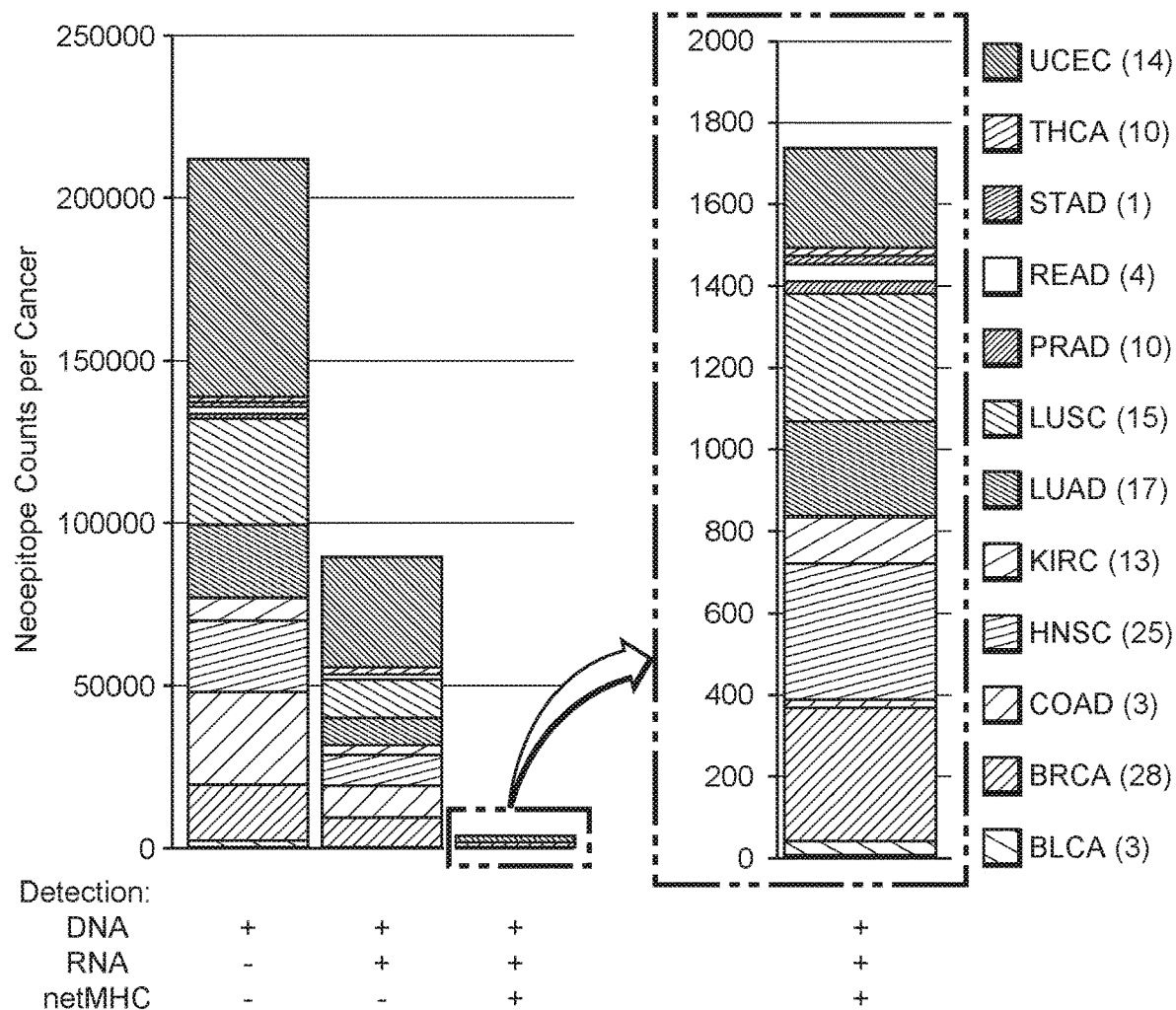
FIG. 2 is an exemplary graphical representation of the frequency for HLA-matched neoepitopes for various cancers, as well as a graphical representation of frequency of unique neoepitopes within cancer driving genes.
Figure 2:
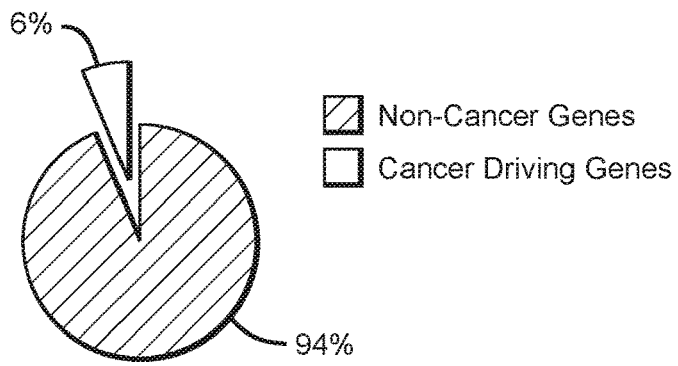

Using the TCGA dataset and the methods described above, the inventors filtered neoepitopes by tumor versus normal (DNA+), expressed tumor versus normal (DNA+, RNA+), and expressed and HLA-matched tumor versus normal (DNA+, RNA+, netMHC+). Here, the inventors limited the analysis to samples containing the HLA-A*02:01 allele, which occurs in high frequencies across North America. Notably, and as is graphically shown in FIG. 2, the numbers of predicted neoepitopes, expressed neoepitopes, and neoepitopes with affinity to HLA-A*02:01 were 211, 285, 89,351, and 1,732, respectively. Correcting for different sample sizes, the average number of predicted neoepitopes, expressed neoepitopes, and neoepitopes with affinity to HLA-A*02:01 were 23,272, 9,619, and 138, respectively. The unfiltered and filtered neoepitopes were then analyzed for their location within a desired gene type (here: cancer driver genes) using a collection of known cancer driver genes as described above. Interestingly, and as is shown in the pie graph of FIG. 2, across all cancers only 6% of neoepitopes occurred in cancer driver genes, which further helps reduce an otherwise confusingly large number of potential targets to a relatively low number of targets with potentially high impact. Moreover, especially in cases where the number of filtered neoepitopes is relatively low, identification of a cancer driver neoepitopes will present an opportunity for selection of a neoepitope for treatment that would otherwise not be realized.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a cancer in a patient using immune therapy, comprising:
    obtaining from a patient omics data from a tumor tissue and a matched normal tissue, and using the omics data to determine a plurality of expressed missense based patient- and tumor-specific neoepitopes;
    deriving from the expressed missense based patient- and tumor-specific neoepitopes a cancer driver neoepitope; and
    administering to the patient an immune therapeutic agent that comprises a synthetic antibody having binding specificity to the cancer driver neoepitope.

2. The method of claim 1 wherein the step of determining the plurality of expressed missense based patient- and tumor-specific neoepitopes comprises location-guided synchronous alignment of omics data from the tumor tissue and the matched normal tissue.

3. The method of claim 1 further comprising a step of filtering the expressed missense based patient- and tumor-specific neoepitopes by at least one of an a priori known molecular variation selected from the group consisting of a single nucleotide polymorphism, a short deletion and insertion polymorphism, a microsatellite marker, a short tandem repeat, a heterozygous sequence, a multinucleotide polymorphism, and a named variant.

4. The method of claim 1 wherein the tumor tissue is a solid tumor tissue and wherein the matched normal tissue is blood.

5. The method of claim 1 wherein the step of deriving the cancer driver neoepitope comprises a step of filtering the patient- and tumor-specific neoepitopes by HLA type of the patient.

6. The method of claim 5 wherein the step of filtering by HLA type uses a plurality of distinct individual neoepitope sequences in which a changed amino acid has a distinct position within the neoepitope sequence, and wherein the individual neoepitope sequences have a length of between 7 and 20 amino acids.

7. The method of claim 5 wherein the step of filtering by HLA type comprises determination of the HLA type from the patient omics data.

8. The method of claim 5 wherein the step of filtering by HLA type is performed to a depth of at least 4 digits.

9. The method of claim 5 wherein the step of filtering by HLA type comprises determination of affinity of the neoepitopes to at least one MHC Class I sub-type and to at least one MHC Class II sub-type of the patient.

10. The method of claim 1 wherein the cancer driver neoepitope is located in a gene selected from the group consisting of ALL, AML, BLCA, BRCA, CLL, CM, COREAD, ESCA, GBM, HC, HNSC, LUAD, LUSC, MB, NB, NSCLC, OV, PRAD, RCCC, SCLC, STAD, THCA, and UCEC.

11. The method of claim 1 wherein the cancer driver gene comprises AURKA, BAP1, BRCA1, BRCA2, CCND3, CCNE1, CDK4, CDK6, CDKN1B, CDKN2A, CDKN2B, EGFR, ERBB2, FBXW7, FGFR1, FGFR2, FGFR3, IGF1R, MDM2, MDM4, MET, NF1, NF2, PTEN, SMARCA4, SMARCB1, STK11, and/or TP53.

12. The method of claim 1 further comprising a step of administering a non-immune therapeutic drug that targets a protein comprising the cancer driver neoepitope.

* * * * *